US012811001B2

(12) United States Patent
Venkataraman et al.

(10) Patent No.: US 12,811,001 B2
(45) Date of Patent: Nov. 24, 2026

(54) METHOD AND SYSTEM FOR EXTRACTING AN ACTUAL SURGICAL DURATION FROM A TOTAL OPERATING ROOM (OR) TIME OF A SURGICAL PROCEDURE

(71) Applicant: Verb Surgical Inc., Santa Clara, CA (US)

(72) Inventors: Jagadish Venkataraman, Menlo Park, CA (US); Pablo Garcia Kilroy, Menlo Park, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 19/274,346

(22) Filed: Jul. 18, 2025

(65) Prior Publication Data

US 2026/0018277 A1 Jan. 15, 2026

Related U.S. Application Data

(63) Continuation of application No. 18/338,957, filed on Jun. 21, 2023, now Pat. No. 12,367,970, which is a (Continued)

(51) Int. Cl.
*G16H 40/20* (2018.01)
*A61B 34/10* (2016.01)
(Continued)

(52) U.S. Cl.
CPC ............. *G16H 40/20* (2018.01); *A61B 34/10* (2016.02); *G06N 20/00* (2019.01); *G16H 40/40* (2018.01)

(58) Field of Classification Search
None
See application file for complete search history.

(56) References Cited

U.S. PATENT DOCUMENTS 7,317,955 B2 1/2008 McGreevy
10,383,694 B1 8/2019 Venkataraman et al.
(Continued)

FOREIGN PATENT DOCUMENTS

CN 103299355 A 9/2013
CN 104758051 A 7/2015
(Continued)

OTHER PUBLICATIONS

Akhavan, Sina, "Time-driven Activity-based Costing More Accurately Reflects Costs in Arthroplasty Surgery," Clin Orthop Relat Res (2016) 747:8-15 (Year: 2016).*
(Continued)

*Primary Examiner* — John P Go
(74) *Attorney, Agent, or Firm* — Aikin & Gallant, LLP

(57) ABSTRACT

Embodiments described herein provide various examples of a system for extracting an actual procedure duration composed of actual surgical tool-tissue interactions from an overall procedure duration of a surgical procedure on a patient. In one aspect, the system is configured to obtain the actual procedure duration by: obtaining an overall procedure duration of the surgical procedure; receiving a set of operating room (OR) data from a set of OR data sources collected during the surgical procedure, wherein the set of OR data includes an endoscope video captured during the surgical procedure; analyzing the set of OR data to detect a set of non-surgical events during the surgical procedure that do not involve surgical tool-tissue interactions; extracting a set of durations corresponding to the set of non-surgical events; and determining the actual procedure duration by subtracting the set of extracted durations from the overall procedure duration.

18 Claims, 6 Drawing Sheets

Related U.S. Application Data continuation of application No. 17/146,823, filed on Jan. 12, 2021, now Pat. No. 11,728,029, which is a continuation of application No. 16/221,045, filed on Dec. 14, 2018, now Pat. No. 10,910,103.

(51) Int. Cl.
*G06N 20/00* (2019.01)
*G16H 40/40* (2018.01)

(56) References Cited

U.S. PATENT DOCUMENTS

| | | | |
|---|---|---|---|
| 2002/0013512 | A1 | 1/2002 | Sendai et al. |
| 2009/0125337 | A1 | 5/2009 | Abri |
| 2010/0228264 | A1 | 9/2010 | Robinson et al. |
| 2012/0253892 | A1 | 10/2012 | Davidson |
| 2013/0021813 | A1 | 1/2013 | Godbillon |
| 2013/0218137 | A1 | 8/2013 | Abovitz et al. |
| 2013/0304347 | A1 | 11/2013 | Davidson |
| 2014/0018637 | A1 * | 1/2014 | Bennett ............... H04L 43/0817 607/51 |
| 2014/0081659 | A1 | 3/2014 | Nawana et al. |
| 2014/0287393 | A1 | 9/2014 | Kumar et al. |
| 2014/0288365 | A1 | 9/2014 | Henley et al. |
| 2015/0297807 | A1 | 10/2015 | Leblanc et al. |
| 2016/0307950 | A1 | 10/2016 | Huang et al. |
| 2016/0379504 | A1 | 12/2016 | Bailey et al. |
| 2017/0000564 | A1 | 1/2017 | Gordon et al. |
| 2017/0105621 | A1 * | 4/2017 | Pratt ...................... G16H 50/20 |
| 2018/0028088 | A1 * | 2/2018 | Garbey .................. A61B 34/20 |
| 2018/0110398 | A1 * | 4/2018 | Schwartz ............. A61B 1/0002 |
| 2018/0122506 | A1 * | 5/2018 | Grantcharov ....... H04L 63/0421 |
| 2019/0362834 | A1 | 11/2019 | Venkataraman et al. |
| 2020/0285771 | A1 | 9/2020 | Dey et al. |
| 2022/0005332 | A1 | 1/2022 | Metzler et al. |

FOREIGN PATENT DOCUMENTS

| | | | |
|---|---|---|---|
| WO | 2010111523 | A1 | 9/2010 |
| WO | 2014043661 | A1 | 3/2014 |
| WO | 2016149794 | A1 | 9/2016 |
| WO | 2017098504 | A9 | 6/2017 |

OTHER PUBLICATIONS

Bouarfa, Loubna, "In-vivo real-time tracking of surgical instruments in endoscopic video," Minimally Invasive Therapy, 2012;21:129-134 (Year: 2012).*

Richards, C., "Skills evaluation in minimally invasive surgery using force/torque signatures," Surg Endosc (2000) 14: 791-798 (Year: 2000).*

Final Office Action received for U.S. Appl. No. 18/338,957, mailed on Nov. 6, 2024, 15 pages.

Notice of Allowance received for U.S. Appl. No. 18/338,957, mailed on Apr. 1, 2025, 13 pages.

Office Action received for European Application No. 18942874.1, mailed on Mar. 5, 2026, 6 pages.

Supplementary European Search Report and Search Opinion received for EP Application No. 18942874.1, mailed on Aug. 9, 2022, 10 pages.

Fairley et al.; "Improving the efficiency of the operating room environment with an optimization and machine learning model," retrieved online: https://pubmed.ncbi.nlm.nih.gov/30387040/DOI: 10.1007/s10729-018-9457-3; Health Care Management Science 2019; 22; Nov. 1, 2018 pp. 756-767.

International Search Report and Written Opinion received for PCT Patent Application No. PCT/US2018/067553, mailed Sep. 17, 2019, 10 pages.

Loubna et al., "In-vivo real-time tracking of surgical instruments in endoscopic video," ISSN 1364-5706; print/ISSN 1365-2931; retrieved online: https://pubmed.ncbi.nlm.nih.gov/21574828/ DOI: 10.3109/13645706.2011.580764; Informa Healthcare; Minimally Invasive Therapy, 2012; 21; pp. 129-134.

Akhavan et al; "Time-driven Activity-based Costing More Accurately Reflects Costs in Arthroplasty Surgery;" Clinical Orthopaedics and Related Research; retrieved online: https://pubmed.ncbi.nlm.nih.gov/25721575/DOI: 10.1007/s11999-015-4214-0; (2016; 474:1); pp. 8-15.

Extended European Search Report received for European Application No. 18942874.1 mailed Aug. 9, 2022, 11 pages.

Richards et al.; "Skills evaluation in minimally invasive surgery using force/torque signatures;" retrieved online: https://DOI.org/10.1007/s004640000230; Surgical Endoscopy (2000; 14:9); pp. 791-798.

Quellec et al.; "Real-Time Task Recognition in Cataract Surgery Videos Using Adaptive Spatiotemporal Polynomials;" retrieved online: https://pubmed.ncbi.nlm.nih.gov/25373078/DOI: 10.1109/TMI.2014.2366726; IEEE Transactions on Medical Imaging (2015: 34:4); pp. 877-887.

International Preliminary Report on Patentability received for PCT Patent Application No. PCT/US2018/067553 mailed Jun. 8, 2021, 8 pages.

First Office Action received for Chinese Patent Application No. 201880100680.0, mailed on Mar. 21, 2024, 18 pages (9 pages of English Translation and 9 pages of Original Document).

Second Office Action received for Chinese Patent Application No. 201880100680.0, mailed on Sep. 25, 2023, 10 pages (5 pages of English Translation and 5 pages of Original Document).

Notice of Allowance received for U.S. Appl. No. 16/221,045, mailed Sep. 30, 2020, 15 pages.

Non-Final Office Action received for U.S. Appl. No. 17/146,823, mailed Dec. 21, 2022, 12 pages.

Non-Final Office Action received for U.S. Appl. No. 18/338,957, mailed Jul. 11, 2024, 15 pages.

* cited by examiner

EXEMPLARY FULL SURGICAL PROCEDURE 200

METHOD AND SYSTEM FOR EXTRACTING AN ACTUAL SURGICAL DURATION FROM A TOTAL OPERATING ROOM (OR) TIME OF A SURGICAL PROCEDURE

PRIORITY CLAIM AND RELATED PATENT APPLICATIONS

This patent application is a continuation of, and hereby claims the benefit of priority under 35 U.S.C. § 120 to U.S. patent application Ser. No. 18/338,957, filed on Jun. 21, 2023, entitled "Method and System for Extracting an Actual Surgical Duration from a Total Operating Room (OR) Time of a Surgical Procedure," by inventors Jagadish Venkataraman and Pablo Garcia Kilroy, now U.S. Pat. No. 12,367,970, issued Jul. 22, 2025, which is a continuation of U.S. patent application Ser. No. 17/146,823, filed on Jan. 12, 2021, entitled "Method and System for Extracting an Actual Surgical Duration from a Total Operating Room (OR) Time of a Surgical Procedure," by inventors Jagadish Venkataraman and Pablo Garcia Kilroy, now U.S. Pat. No. 11,728,029, issued Aug. 15, 2023, which is a continuation of U.S. patent application Ser. No. 16/221,045, filed on Dec. 14, 2018, entitled, "Method and System for Extracting an Actual Surgical Duration from a Total Operating Room (OR) Time of a Surgical Procedure," by inventors Jagadish Venkataraman and Pablo Garcia Kilroy, now U.S. Pat. No. 10,910,103, issued on Feb. 2, 2021, all of which are incorporated herein by reference in their entirety.

TECHNICAL FIELD

The present disclosure generally relates to building machine-learning-based surgical procedure analysis tools and, more specifically, to systems, devices and techniques for extracting an actual surgical duration from a total operating room (OR) time of a surgical procedure based on multiple sources of data collected during the surgical procedure.

BACKGROUND

Operating room (OR) costs are among the highest medical and healthcare-related costs. With skyrocketing healthcare expenditures, OR-costs management aimed at reducing OR costs and increasing OR efficiency has become an increasingly important research subject. OR costs are often measured based on a per-minute cost structure. For example, one 2005 study shows that the OR costs range from $22 to $133 per minute with an average cost of $62 per minute. In this per-minute cost structure, the OR costs of a given surgical procedure are directly proportional to the duration/length of the surgical procedure. Hence, OR time-management and scheduling plays a central role in overall OR-costs management. Clearly, OR time-management and scheduling are highly dependent on the duration of a particular type of surgical procedure (also referred to as "procedure time"). For example, OR time for a particular type of surgical procedure can be allocated based on an average duration of that surgical procedure. While predicting the average duration of a given surgical procedure can be a complex task, it is possible to collect a large amount of surgical-procedure-related data and estimate the average duration for the given surgical procedure based on data analyses.

In some conventional surgical procedure analyses, the duration of a surgical procedure is simply measured as a time period between the moment when the patient arrives at the OR (i.e., wheeled-in time) and the moment when the patient leaves the OR (i.e., wheeled-out time). Based on these analyses, a first surgical procedure of a given type performed by a first surgeon may have a total OR time of 50 minutes between the wheeled-in time and the wheeled-out time, while a second surgical procedure of the same type performed by a second surgeon may have a total OR time of one hour and five minutes. When comparing these two surgical procedures, one may conclude that the first surgeon is far more efficient than the second surgeon. However, evaluating surgeon skill/efficiency or an overall OR efficiency based on comparing the total OR times can be extremely flawed. This is because a total OR time of a surgical procedure is typically composed of various segments/events, and the amount of time the surgeon is actually operating on the patient with surgical tools is only one part of the total OR time. In the above-described example, the two surgeons can have substantially the same efficiency, while the time difference in the total OR times can be caused by the inefficiency of the support team of the second surgeon, e.g., when performing tool exchanges. In this case, the times that the surgeon waits for the right tools to be brought in contribute to the total OR time, but are not part of the actual surgical duration.

Some advanced ORs have a multitude of sensors and cameras installed for monitoring OR efficiency. However, these sensors and cameras are primarily used for monitoring patient and surgical staff movements inside the OR and identifying OR efficiency based on the observed movements. Unfortunately, there are no known data analysis tools that perform root-cause analysis on OR videos and sensor data to determine the root causes of OR inefficiency that lead to long total OR times.

SUMMARY

In this patent disclosure, various examples of a surgical procedure analysis system for breaking down a total operating room (OR) time of a surgical procedure into a series of identifiable events, categorizing the events, and determining the duration of each of the identifiable events are disclosed. In particular, these identifiable events can include a set of "non-surgical events" that do not involve interactions between surgical tools and the patient's tissues (i.e., when the surgeon is not performing actual surgical tasks on the patient). For example, the set of non-surgical events can include but are not limited to: "patient preparations" before and after the actual surgical procedure; "out-of-body events" when the endoscope is taken outside of the patient's body for various reasons; "tool exchange events" when one actively used surgical tool is being replaced with another surgical tool and the associated wait times; and "surgical timeout events" when the surgeon pauses for various reasons and is not performing actual surgical tasks on the patient. Moreover, the identifiable events also include a set of actual surgical segments separated by the set of non-surgical events and involving interactions between surgical tools and the patient's tissues (i.e., when the surgeon is performing actual surgical tasks on the patient). Consequently, the actual surgical procedure duration (or "actual procedure duration"), i.e., the actual amount of time the surgeon interacts with the patient's tissues using surgical tools, can be extracted from the total OR time by subtracting/excluding from the total OR time those non-surgical events that do not involve interactions between surgical tools and the patient's tissues.

In various embodiments, the disclosed surgical procedure analysis system identifies various non-surgical events from the total OR time by analyzing one or multiple of the following data sources collected during the total OR time: one or more endoscope videos; recorded OR videos from wall/ceiling cameras; pressure sensors at the doorway of the OR; pressure sensors on the surgical platform; pressure sensors on the tips or jaws of the surgical tools; and/or recorded OR audios. In various embodiments, the disclosed surgical procedure analysis system includes machine-learning modules that can be applied to one or more of the above data sources to identify both non-surgical events and surgical events. In particular, the disclosed surgical procedure analysis system can include machine-learning modules for identifying out-of-body events based on endoscope videos; machine-learning modules for identifying tool exchange events based on endoscope videos; machine-learning modules for identifying surgical timeout events based on endoscope videos; and machine-learning modules for identifying actual surgical segments based on endoscope videos.

In some embodiments, the various predictions made based on endoscope videos can be combined with other data sources to improve the confidence levels of the predictions. For example, the actual surgical segment predictions made based on endoscope videos can be combined with data from pressure sensors on the surgical tool tips/jaws to improve the confidence levels of the predictions. As another example, the out-of-body event predictions based on endoscope videos can be combined with videos from the wall/ceiling cameras to improve the confidence levels of the predictions.

In various embodiments, the disclosed surgical procedure analysis system can also include machine-learning modules for tracking personnel movements inside the OR based on videos from wall/ceiling cameras; machine-learning modules for identifying certain out-of-body events based on videos from wall/ceiling cameras; and machine-learning modules for identifying certain surgical timeout events based on videos from wall/ceiling cameras (e.g., a wait time for a collaborating surgeon to arrive). In some embodiments, the disclosed surgical procedure analysis system can also include machine-learning modules for determining wheeled-in and wheeled-out times based on pressure sensors at the doorway of the OR; machine-learning modules for determining certain timeout events (e.g., repositioning of the surgical tools) based on pressure sensors on the surgical platform; and machine-learning modules for determining certain timeout events (e.g., delays caused by OR room chats/discussions) based on audios recorded in the OR.

In one aspect, a process extracting an actual procedure duration composed of actual surgical tool-tissue interactions from an overall procedure duration of a surgical procedure on a patient is disclosed. This process can begin by obtaining the overall procedure duration of the surgical procedure performed by a surgeon on the patient. The process then receives a set of operating room (OR) data from a set of OR data sources collected during the surgical procedure, wherein the set of OR data includes an endoscope video captured during the surgical procedure. Next, the process analyzes the set of OR data to detect a set of non-surgical events during the surgical procedure that do not involve surgical tool-tissue interactions. For example, analyzing the set of OR data includes performing a machine-learning-based analysis on the endoscope video. The process then extracts a set of durations corresponding to the set of non-surgical events. Finally, the process determines the actual procedure duration by subtracting the set of durations corresponding to the set of non-surgical events from the overall procedure duration.

In some embodiments, the set of OR data further includes one or more of the following: a set of sensor data collected inside the OR during the surgical procedure; a set of audio files recorded inside the OR during the surgical procedure; and one or more videos captured by one or more wall and/or ceiling cameras inside the OR during the surgical procedure.

In some embodiments, the set of sensor data further includes one or more of the following: pressure sensor data collected from surgical tools involved in the surgical procedure; pressure sensor data collected from a surgical platform inside the OR; and pressure sensor data collected from a doorway of the OR.

In some embodiments, the process analyzes the set of OR data to identify a surgical timeout event, wherein a surgical timeout event occurs within a surgical phase of the surgical procedure when the surgeon pauses performing surgical tasks on the patient for a certain time period.

In some embodiments, the process identifies the surgical timeout event by performing a machine-learning-based analysis on the endoscope video to determine that the movement of a surgical tool in the endoscope video has stopped for more than a predetermined time period.

In some embodiments, the process extracts the duration of the identified surgical timeout event by: extracting an initial time of the identified surgical timeout event when the movement of the surgical tool is determined to have stopped based on the machine-learning-based analysis; and extracting an end time of the identified surgical timeout event when the movement the surgical tool is determined to have resumed based on the machine-learning-based analysis.

In some embodiments, the process collaborates the extracted initial time and end time of the identified surgical timeout event with pressure sensor data collected from a pressure sensor located at the tip of the surgical tool.

In some embodiments, the process collaborates the extracted initial time and end time with the pressure sensor data by: collaborating the extracted initial time with a first time when the pressure sensor data decreases to substantially zero; and collaborating the extracted end time with a second time when the pressure sensor data increases from substantially zero to a significant value.

In some embodiments, the surgical timeout event occurs for one of the following set of reasons: (1) when the surgeon stops interacting with the patient and starts a discussion with another surgeon, the surgical support team, or a resident surgeon; (2) when the surgeon pauses to make a decision on how to proceed with the surgical procedure based on an on-screen event or a surgical complication; and (3) when the surgeon pauses to wait for a collaborating surgeon to come into the OR.

In some embodiments, the process analyzes the set of OR data to further identify a set of out-of-body (OOB) events, wherein an OOB event begins when an endoscope used during the surgical procedure is taken out of the patient's body for one of a set of reasons and ends when the endoscope is being inserted back into the patient's body.

In some embodiments, the process identifies an OOB event by performing a machine-learning-based analysis on the endoscope video to (1) identify the beginning of the OOB event based on a first sequence of video images in the endoscope video, and (2) identify the end of the OOB event based on a second sequence of video images in the endoscope video.

In some embodiments, a given OOB event occurs because of one of a following set of reasons: cleaning the endoscope lens when an endoscopic view is partially or entirely blocked; changing the endoscope lens from one scope size to another scope size; and switching the surgical procedure from a robotic surgical system to a laparoscopic surgical system.

In some embodiments, analyzing the set of OR data to detect a set of non-surgical events during the surgical procedure further includes identifying a pre-surgery patient preparation time prior to the surgical procedure and identifying a post-surgery patient assistant time after the completion of the surgical procedure.

In some embodiments, the process obtains the overall procedure duration of the surgical procedure by determining a time when the patient is being wheeled into the OR and a time when the patient is being wheeled out of the OR.

In another aspect, a process extracting an actual procedure duration composed of actual surgical tool-tissue interactions from an overall procedure duration of a surgical procedure on a patient is disclosed. This process can begin by obtaining the overall procedure duration of the surgical procedure performed by a surgeon on the patient. The process then receives a set of operating room (OR) data from a set of OR data sources collected during the surgical procedure, wherein the set of OR data includes an endoscope video captured during the surgical procedure. Next, the process analyzes the set of OR data to detect a set of non-surgical events during the surgical procedure that do not involve surgical tool-tissue interactions. For example, analyzing the set of OR data includes collaborating the endoscope video with the set of sensor data. The process then extracts a set of durations corresponding to the set of non-surgical events. Finally, the process determines the actual procedure duration by subtracting the set of durations corresponding to the set of non-surgical events from the overall procedure duration.

In some embodiments, the set of sensor data further includes one or more of the following: pressure sensor data collected from surgical tools involved in the surgical procedure; pressure sensor data collected from a surgical platform inside the OR; and pressure sensor data collected from a doorway of the OR.

In some embodiments, the set of OR data further includes a set of audio files recorded inside the OR during the surgical procedure and one or more videos captured by one or more wall and/or ceiling cameras inside the OR during the surgical procedure.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Figure 1:
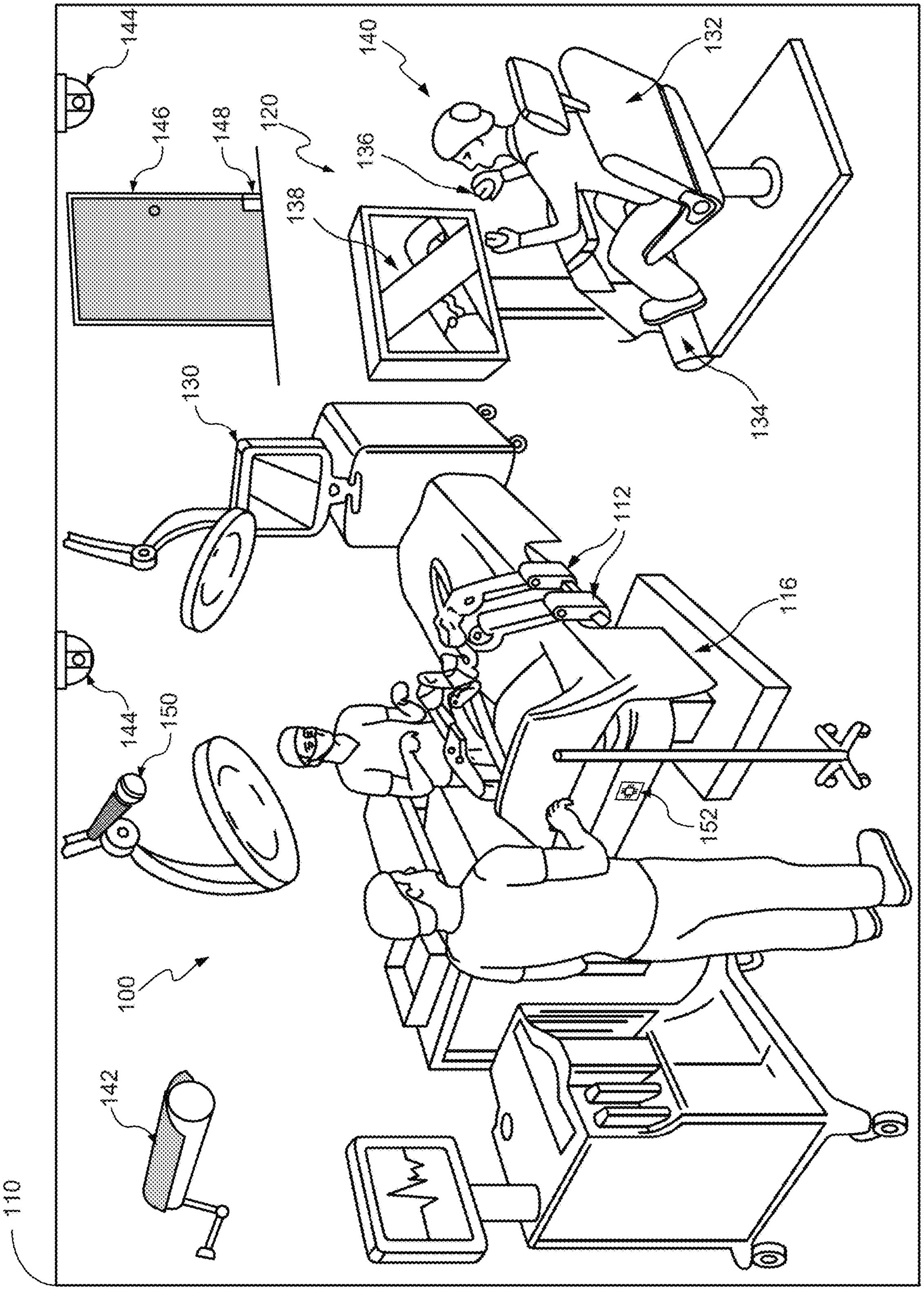
FIG. 1 shows a diagram illustrating an exemplary operating room (OR) environment with a robotic surgical system in accordance with some embodiments described herein.

FIG. 1 shows a diagram illustrating an exemplary operating room (OR) environment 110 with a robotic surgical system 100 in accordance with some embodiments described herein. As shown in FIG. 1, robotic surgical system 100 comprises a surgeon console 120, a control tower 130, and one or more surgical robotic arms 112 located at a robotic surgical platform 116 (e.g., a table or a bed, etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., tele-operation). User console 120 may be located in the same operating room as robotic surgical system 100, as shown in FIG. 1. In other environments, user console 120 may be located in an adjacent or nearby room, or tele-operated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to receive anesthesia. Initial access to the surgical site may be performed manually with robotic surgical system 100 in a stowed or withdrawn configuration to facilitate access to the surgical site. Once the access is completed, initial positioning and/or preparation of the robotic system may be performed. During the procedure, a surgeon in the user console 120 may utilize the foot-operated controls 134 and/or UIDs 136 to manipulate various surgical tools/end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures, including but not limited to, robotic surgical system 100 cleaning and/or sterilization, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit the robotic control commands to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

In addition to robotic surgical system 100, OR environment 110 also includes a wall camera 142 and multiple ceiling cameras 144. During an OR procedure, these cameras can capture staff movements, surgeon movements, activities over surgical platform 116, and movements at a doorway 146 of the OR. Hence, the videos captured by wall camera 142 and ceiling cameras 144 during the OR procedure can provide direct visual information related to surgical staff performance, patient preparations before and after a surgical procedure, surgical tool exchanges, endoscope lens exchanges and cleaning, surgeons taking timeouts, and waiting for a collaborating surgeon, among others. OR environment 110 can also include voice recording devices such as a microphone 150. During an OR procedure, microphone 150 can record audio feeds within OR environment 110 including discussions between surgeons and other people inside or outside OR environment 110.

Various sensors can be installed within OR environment 110 to provide additional information related to surgical procedures taking place inside OR environment 110. For example, OR environment 110 can include pressure sensors 148 installed at doorway 146 that can be used to estimate the times when the patients are being wheeled into and wheeled out of OR environment 110. OR environment 110 also includes pressure sensors 152 installed on surgical platform 116 that can detect events when patients are being transferred onto and removed from surgical platform 116, as well as events when patients are being repositioned on surgical platform 116 during surgical procedures for various purposes, such as creating a new port in the patient's body to allow for better tool access. Although not visible in FIG. 1, surgical tools/end effectors attached to robotic arms 112 can include pressure sensors on the tool tips or jaws of the tools that can detect events when the tools are actually interacting with tissues, and events when the tools are inside the patient's body but idle for various reasons.

In addition to the various data sources within OR environment 110 described above, full surgical procedure videos captured by endoscope cameras remain one of the most important data sources for analyzing surgical procedures, such as estimating the actual duration of the surgical procedure (or "actual procedure duration" hereinafter). Actual procedure duration can be considered as the amount of time the surgeon is actually operating on the patient by manipulating the surgical tools. Hence, the actual procedure duration includes the times that involve tool-tissue interactions, i.e., when the surgical tools actually interact with the tissues. However, the total recorded OR time (or "the total OR time") for a given surgical procedure is typically measured from the moment the patient is wheeled into the OR to the moment the patient is wheeled out of the OR. We also refer to the entire OR process corresponding to this total recorded OR time as "the overall surgical procedure" or "the full surgical procedure" hereinafter.

Note that the total OR time can include various time periods during which no tool-tissue interactions take place. For example, these time periods can be associated with the surgeon waiting for a tool to be brought in, taking a timeout to discuss with his surgical team, taking the endoscope out of the patient's body to be cleaned, and so on. As such, the actual procedure duration is generally not continuous but segmented by a set of non-tool-tissue-interaction events (or "non-surgical events" for simplicity) during which time the surgeon is not applying surgical tools on the tissues and, hence, no tool-tissue interaction is taking place. By definition, the total OR time is the sum of the combined time of all of these non-surgical events and the above-described actual procedure duration. Consequently, if these non-surgical events can be identified within the total OR time and their durations extracted, the actual procedure duration can be determined by excluding the combined time of these non-surgical events from the total OR time.

Some embodiments described herein aim to detect these non-surgical events by combining various available data sources within the OR including procedure videos from endoscope cameras, OR videos from the wall cameras and/or ceiling cameras, and various sensor data from the OR including: data from pressure sensors on the doors of the OR, data from pressure sensors on the surgical platforms, and data from pressure sensors on the tips of the surgical tools, among others. In various embodiments, the above-described data sources can be analyzed/mined using various machine-learning-based techniques, conventional computer-vision techniques such as image processing, or a combination of machine-learning and computer-vision techniques to identify these non-surgical events and extract the associated event durations. We now describe different types of the non-surgical events in more detail below.

Patient Preparation before the Surgical Procedure

This is a time period when the surgical staff prepares the patient for surgery, after the patient has been wheeled into the OR. The time period can include transferring the patient from the wheeled bed onto the surgical platform, positioning the patient on the surgical platform for convenient surgical tool access, arranging patient's clothing for surgical tool access, preparing the patient's skin for incision, and positioning the surgical tools over the patient's body, among other things. Note that during this preparation time no endoscope video is available because the endoscope camera has not been introduced into the patient's body. We also refer to this time period as the "pre-surgery preparation time" or "the first patient preparation time" hereinafter.

Tool Exchange Times/Events

A tool exchange event is a time period when one actively used surgical tool is being replaced with another surgical tool. More specifically, during a tool exchange time/event, the actively used surgical tool is being taken out of the patient's body and the next surgical tool is being brought into the patient's body. Note that, in addition to the time needed to remove one tool and bring in another tool, the tool exchange time can also include time that the surgeon waits for the new tool. This wait time can be affected by the readiness of the surgical support team in the OR. It is appreciated that, a surgical support team that understands the surgeon's technique and tool needs can have the right tool supplies available at the right times for tool exchange to happen smoothly. In contrast, if the surgical support team changes due to absence of some personnel, it is common for surgeons to wait around for the right tool to show up, which can be retrieved from the inventory outside of the OR during the surgical procedure. Other factors that can contribute to the wait time during tool exchange include: time to sterilize the new tool (if the tool is not sterilized); time to open a new tool; and time to warm up a new tool (a cold tool cannot be inserted into a patient's body because the patient can go into shock).

In some embodiments, tool exchange times can be detected based on the endoscope videos, because during a tool exchange event the endoscope generally remains inside the patient's body and continues to record. For example, the beginning of a tool exchange event can be identified when it is detected that an actively used tool disappears from the video images; and the end of a tool exchange event can be identified when it is detected that a new tool appears in the video images. Because detecting a tool exchange event involves detecting and recognizing multiple surgical tools, a machine-learning based analysis can be applied to the endoscope videos, e.g., by identifying the beginning of the tool exchange event based on a first sequence of video images and identifying the end of the tool exchange event based on a second sequence of video images.

In other embodiments, tool exchange times can be detected based on OR videos from wall and ceiling cameras or based on the pressure sensor data from the tips or the jaws of the two surgical tools involved in the tool exchange event. However, the tool exchange times can be detected and durations inferred mainly based on the endoscope videos; the predictions made based on endoscope videos can be combined with OR videos from wall and ceiling cameras and/or pressure sensor data from the tips or the jaws of the surgical tools to improve the confidence levels of the predictions.

Out-of-Body (OOB) Times/Events

An OOB time/event is generally defined as a time period when the endoscope is taken out of the patient's body for one of various reasons during the surgical procedure while the endoscope camera continues to record, or right before and/or right after the surgical procedure while the endoscope camera is recording, so that the endoscope video is available for analysis. An initial OOB time/event can exist at the beginning of a surgical procedure if the endoscope camera is turned on prior to being inserted into the patient's body; and a final OOB time/event can exist at the end of a surgical procedure if the endoscope camera remains turned on for a period of time after the completion of the surgical procedure when the endoscope camera has been taken out of the patient's body.

During the actual surgical procedure, an OOB event can take place for a number of reasons. For example, an OOB event will occur if the endoscope lens has to be cleaned. Note that a number of surgical events can cause the endoscopic view to be partially or entirely blocked. These surgical events can include, but are not limited to: (a) endoscope lens is covered with blood and visibility is partially or completely lost (e.g., due to a bleeding complication); (b) fogging of the endoscope lens due to condensation, e.g., as a result of the temperature difference between the lens and the patient's body; and (c) endoscope lens is covered with cautery-generated tissue particles, which stick to the lens and eventually block the endoscopic view. In each of the above scenarios, the endoscope camera needs to be taken out of the body so that the endoscope lens can be cleaned to restore visibility or warmed up for condensation removal. After cleaning and/or other necessary treatment, the endoscope camera often needs to be re-calibrated, including performing white-balancing before it can be put back into the patient's body, which takes additional time to complete. Note that this lens-cleaning type of OOB event can take a few minutes to complete.

As another example of a different type of OOB event, sometimes during a surgical procedure, the endoscope lens needs to be changed from one scope size to another scope size for different anatomy/fields of view (FOV). For example, a surgical procedure may first use a smaller scope size (i.e., 5 mm)/larger FOV endoscope lens to locate a difficult-to-find anatomy, and then change to a larger scope size (i.e., 10 mm)/smaller FOV endoscope lens to perform the actual operation on the specific anatomy. In such events, the endoscope camera needs to be taken out of the patient's body so that the scope can be changed. After changing the scope, the endoscope camera often needs to be re-calibrated, including performing white-balancing before it can be inserted back into the patient's body, which takes additional time to complete.

As yet another example of another type of OOB event, some robotic surgical procedures today are not 100% robotic, but with a majority (e.g., 90%) of a given procedure performed with a robotic system and a small portion (e.g., 10%) of the given procedure still performed with a laparoscopic system. In such a hybrid surgical procedure, there is a transition or downtime during the overall procedure when the robotic system is disengaged (including removing the endoscope camera) and laparoscopic tools are engaged (including introducing the laparoscopic camera). Depending on the efficiency and skills of the surgical support team, the transition requires a certain amount of time to move the robot away (including disengaging the robot arms), engage the laparoscopic tools, and wait for the laparoscopic surgeon to arrive at the OR. Note that the beginning of this transition time can be identified as the moment that the endoscope video stops, while the end of the transition time can be identified as the moment that the laparoscopic camera images begin to show. Moreover, this OOB event can be easily identifiable and therefore distinguishable from other OOB events without system changes because the view of the laparoscopic images is typically quite different from the view of the endoscope images. For example, the endoscope view is usually quite zoomed in so that the anatomy often occupies the full screen, whereas the laparoscopic view is usually circular surrounded by a black border on the screen.

Surgical Timeout Events

Surgical timeout events, or simply "surgical timeouts," can include various times/events taking place during the surgical procedure when the surgeon pauses for various reasons and is not performing actual surgical tasks on the patient. While there can be different types of surgical timeout events for different reasons, each of the surgical timeout events can be identified based on the fact that the endoscope images become "static," i.e., show a lack of meaningful movement. In particular, if there were one or more surgical tools within the field of view, the tools would have substantially stopped moving. Note that for certain time periods during which the associated endoscope video images do not contain any surgical tools, these time periods can also be considered as surgical timeouts. However, if such a time period is part of the above-described tool exchange event (e.g., when the surgeon is waiting for the new tool to arrive), the time period can be identified as part of the tool exchange event instead of a separate surgical timeout event.

As mentioned above, surgical timeouts can be caused by different reasons. Typical surgical timeouts can be caused by, but are not limited to, the following reasons. For example, some surgical timeouts are caused by necessary OR discussions. More specifically, a surgical timeout can occur during the actual surgical procedure when the surgeon stops interacting with the tissue and starts a discussion with another surgeon, the surgical support team, or other residents. These discussions can include discussions for making collective decisions on how to proceed with the procedure under the current situation, such as a complication. These discussions can also include times when the surgeon is teaching the residents who are observing the procedure.

Surgical timeouts can also occur when the surgeons make decisions (on their own or in consultation with the surgical support team) based on on-screen events or complications. For example, there can be time periods during a given procedure when a surgeon has to assess the on-screen events such as comprehending the anatomy, and/or discussing how to deal with complications. During these times, the surgeon is only making decisions, not actually operating on the patient.

On some rare occasions, surgical timeouts can occur when the surgeon becomes lost in the on-screen events such as a complex anatomy and does not know how to proceed. For example, such events can happen when junior surgeons encounter situations they have not experienced before. Such situations can arise either due to taking a wrong step in the procedure or due to an unusual anatomy. To resolve such situations, the surgeon may have to be on a call with a senior surgeon, resort to tele-operation with an expert surgeon, or even look up on the Internet for videos of similar procedures. In any of these scenarios, the surgeon will have to pause to have the situation resolved without actually operating on the patient.

Another type of surgical timeout is caused by waiting for a collaborating surgeon to come into the OR. In complex surgical procedures such as an esophagectomy, there can be multiple surgeons collaborating across different phases of the procedure. In such cases, the appropriate surgeons will need to be paged at the appropriate times. However, even if the next appropriate surgeon is notified at the time when the current phase of the procedure is being completed, it may still take some time for the next surgeon to come to the OR, which can potentially cause delays.

Patient Assistant after the Surgical Procedure

This is the final time period in the total OR time after the last step of the actual surgical procedure has been completed. During this time period the surgical support team performs necessary steps to complete the overall surgical procedure, such as closing up the incisions in the patient, cleaning up the patient's body (e.g., removing an IV line), transferring the patient from the surgical platform to a wheeled bed, and finally wheeling the patient out of the OR, among other things. Note that during this patient assistant time, no endoscope video is available because the endoscope camera has been turned off. We also refer to this time period as the "post-surgery preparation time" or "the second patient preparation time" hereinafter.

In various embodiments, the above-described data sources can be analyzed/mined using various machine-learning-based techniques, conventional computer-vision techniques such as image processing, or a combination of machine-learning and computer-vision techniques to identify these non-surgical events and extract the associated event durations. We now describe different types of the non-surgical events in more detail below.

Some embodiments described in this disclosure aim to combine various available data sources within the OR and analyze these data sources individually or in combination to facilitate detecting the above-described non-surgical events within an overall surgical procedure and determining the associated durations of these events. In various embodiments, the available data sources can be analyzed/mined using various machine-learning-based techniques, conventional computer-vision techniques such as image processing, or a combination of machine-learning and computer-vision techniques to identify these non-surgical events and extract the associated event durations. By combining data from the multiple data sources in the OR, and applying computer-vision and machine-learning techniques to analyze these data, the disclosed technology can reconstruct the actual procedure duration by separating the detected events from the actual procedure duration. Alternatively, the actual procedure duration within the total OR time can be directly determined by analyzing the same data sources, and in doing so, detecting all of the tool-tissue interaction events and extracting the associated durations of the detected tool-tissue interaction events.

Figure 2:
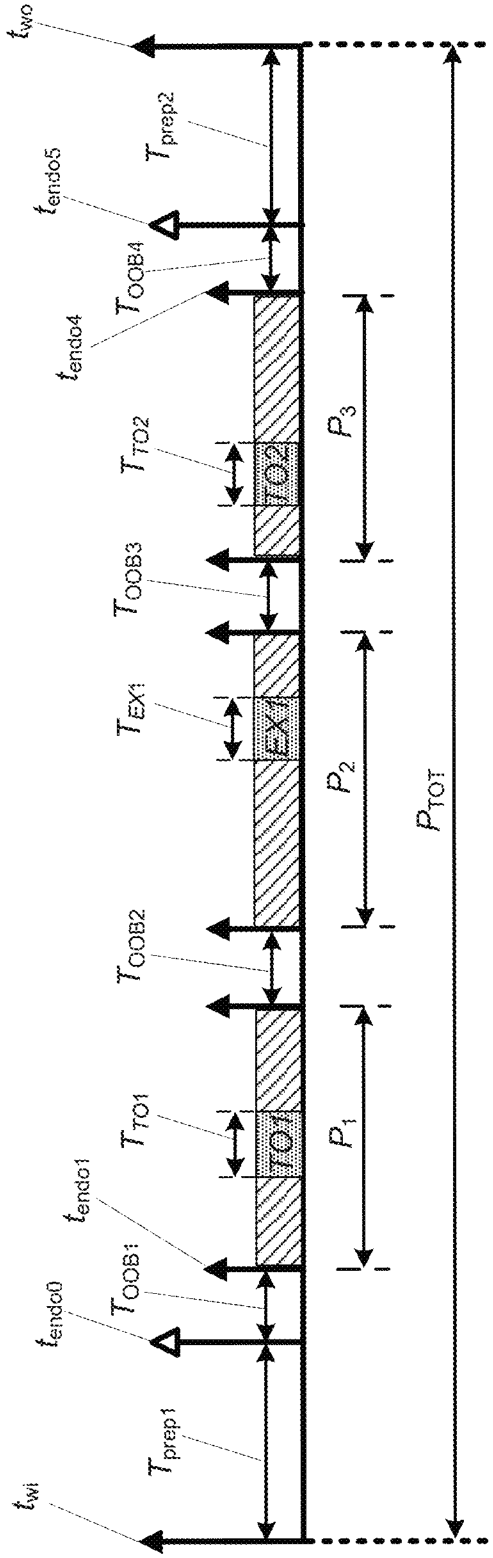
FIG. 2 illustrates a timeline of an exemplary full surgical procedure indicating various surgical and non-surgical events that make up the duration of the full surgical procedure in accordance with some embodiments described herein.

FIG. 2 illustrates a timeline of an exemplary full surgical procedure 200 indicating various surgical and non-surgical events that make up the duration of the full surgical procedure in accordance with some embodiments described herein.

As can be seen in FIG. 2, full surgical procedure 200 starts at the moment the patient is wheeled into the OR, indicated as a timestamp $t_{wi}$, and ends at the moment the patient is wheeled out of the OR, indicated as a timestamp $t_{wo}$. As mentioned above, $t_{wi}$ and $t_{wo}$ can be determined based on data from sensors installed in or near the OR entrance. For example, $t_{wi}$ and $t_{wo}$ can be determined with one or more pressure sensors installed on the floor near the OR entrance by detecting the combined weight of the wheeled bed and the patient on the bed. Alternatively, $t_{wi}$ and $t_{wo}$ can be determined by analyzing videos from the wall camera and/or ceiling cameras that capture the moments of $t_{wi}$ and $t_{wo}$ at the OR entrance. In some embodiments, $t_{wi}$ and $t_{wo}$ can be determined by combining the pressure sensor data at the doorway and the videos from the wall and/or ceiling cameras to increase the confidence level of the estimated $t_{wi}$ and $t_{wo}$.

Still looking at FIG. 2, note that immediately after $t_{wi}$ is the first (i.e., pre-surgery) preparation time $T_{prep1}$. This is the time period when the surgical staff prepares the patient for surgery, such as transferring the patient from the wheeled bed onto the surgical platform, positioning the patient on the surgical platform for convenient surgical tool access, arranging the patient's clothing for surgical tool access, preparing the patient's skin for incision, and positioning the surgical tools over the patient's body, among other things. Note that during preparation time $T_{prep1}$ no endoscope feed is available because the endoscope camera has not been introduced into the patient's body. In some embodiments, the end of preparation time $T_{prep1}$ can be marked as the moment when the first incision (e.g., for the camera port) is made, because this represents the beginning of applying the surgical tools on the patient's body. In these embodiments, the end of preparation time $T_{prep1}$ and the beginning of the endoscope video can have a noticeably short intervening gap. In the embodiment shown in FIG. 2, however, preparation time $T_{prep1}$ ends at the moment when the endoscope video begins, which is designated as $t_{endo0}$. Time point $t_{endo0}$ can also be determined by analyzing the videos from wall and/or ceiling cameras that capture the moment when the first incision on the patient's body is made. Hence, the first preparation time $T_{prep1}$ can be easily determined based on the extracted values of $t_{wi}$ and $t_{endo0}$. In some embodiments, the first preparation time $T_{prep1}$ can be determined by combining the endoscope video and the wall and/or ceiling camera videos.

In some embodiments, if the estimated first preparation time $T_{prep1}$ is significantly longer than a normal pre-surgery preparation time, the wall camera and/or ceiling camera videos can be used to identify the cause(s) of the inefficiency, e.g., based on how the actual preparation progressed and which person or persons were responsible for the delay(s) during the patient preparation.

Note that the endoscope video recording from the endoscope camera can begin before or after the endoscope camera has been inserted into patient's body. Hence, $t_{endo0}$, which represents the beginning of the endoscope video, can occur prior to or after the endoscope camera insertion. For example, if the endoscope camera is turned on before the insertion, $t_{endo0}$ will occur before the insertion. The exemplary surgical procedure 200 illustrates a scenario when $t_{endo0}$ occurs before the insertion when the endoscope camera remains outside of the patient's body. As a result, the time segment immediately following $t_{endo0}$ and right before the insertion represents an OOB event, designated as $T_{OOB1}$. It can be appreciated that $T_{OOB1}$ can be determined simply by analyzing the beginning portion of the endoscope video. As described in more detail below, the full surgical procedure 200 can include multiple OOB events. Note that during these OOB events no tool-tissue interactions take place within the patient's body. Hence, the overall duration of these multiple OOB events can contribute to a significant amount of non-surgical time and, hence, OR inefficiency.

As shown in FIG. 2, the first OOB event $T_{OOB1}$ ends at time $t_{endo1}$, which represents the moment when the endoscope camera is inserted into the camera port in the patient's body and anatomical images inside the patient's body begin to show. The end of $T_{OOB1}$ can also represent the beginning of the actual surgical procedure when the surgical tools are inserted and begin interacting with the tissues. Note that some variations to the exemplary surgical procedure 200 do not have $T_{OOB1}$ if the endoscope camera is turned on during or after the insertion. In these cases, $t_{endo0}$ and $t_{endo1}$ are substantially the same time representing the beginning of the endoscope video.

Still referring to FIG. 2, note that following $t_{endo1}$, i.e., the beginning of the endoscopic video, surgical procedure 200 comprises a sequence of phases designated as $P_1$, $P_2$, and $P_3$. These phases are separated by a sequence of OOB events designated as $T_{OOB2}$, $T_{OOB3}$, and $T_{OOB4}$. More specifically, each of the phases $P_1$, $P_2$, and $P_3$ is defined as a time period when the endoscope video is available while the endoscope camera remains inside the patient's body, while each of the OOB events $T_{OOB2}$, $T_{OOB3}$, and $T_{OOB4}$ is defined as a time period when the endoscope is taken out of the patient's body for various reasons during and immediately after the actual surgical procedure. For example, one of the OOB events $T_{OOB2}$ can correspond to an event when the endoscope is taken out of the body so that the endoscope lens can be cleaned, re-calibrated (e.g., with white balancing), and then re-inserted into the patient's body. During these OOB events, the surgeon performing surgical procedure 200 has to wait for the endoscope and the actual surgical procedure is paused. Consequently, to determine the actual procedure duration, the combined duration of all of these OOB events should be determined and excluded from the overall surgical procedure duration between $t_{wi}$ and $t_{wo}$.

Note that while the exemplary surgical procedure 200 includes four OOB events, other surgical procedures can include a fewer or greater number of OOB events and corresponding time periods. Moreover, the last OOB time period $T_{OOB4}$ takes place toward the end of the surgical procedure 200, which is identified as the time period between a timestamp $t_{endo4}$ corresponding to the moment the endoscope video images from inside of the patient's body end as the endoscope camera is being taken out of the patient's body, and a timestamp $t_{endo5}$ corresponding to the moment the endoscope camera is turned off marking the end of the endoscope video. Similar to the first OOB period $T_{OOB1}$, $T_{OOB4}$ can also be determined simply by analyzing the endoscope video to identify the video image(s) corresponding to $t_{endo4}$. Note that another surgical procedure may not have a corresponding time period like $T_{OOB4}$ if the endoscope camera is turned off prior to or during the removal of the endoscope camera from the patient's body after the completion of the surgical procedure. In such scenarios, the end of the last procedural phase, such as $P_3$ corresponds to the end of the endoscope video.

Note that during each of the phases $P_1$, $P_2$, and $P_3$, a number of other non-surgical events can occur that do not belong to the actual procedure duration but contribute to the overall surgical procedure 200. As mentioned above, these events can include various surgical timeouts, which can include but are not limited to the following types of events: (1) the surgeon is discussing how to proceed with the surgical support team or other residents; (2) the surgeon is teaching the residents; (3) the surgeon is waiting for a collaborating surgeon to arrive; and (4) the surgeon is making a decision based on on-screen events or complications. These additional non-surgical events can also include tool exchange events. On rare occasions, these non-surgical events can also include scenarios when the surgeon is lost in the on-screen anatomy and does not know how to proceed.

As a specific example, phase $P_1$ within the exemplary surgical procedure 200 can include a surgical timeout event $TO_1$ when the surgeon is discussing how to proceed with the surgical support team or residents in the OR. This event $TO_1$ corresponds to a time period designated as $T_{TO1}$. As discussed above, while surgical timeouts can take a number of types or forms, they are typically identifiable in the endoscope video when the surgical tool stops moving. Because event $TO_1$ happens within phase $P_1$ when the endoscope video is available, event $TO_1$ can be detected based on a lack of surgical tool movement. For example, when it is determined that tool movement in the endoscope video has substantially stopped for more than a predetermined time period, the initial time when the movement is determined to have stopped can be recorded as the beginning of the $TO_1$. When the tool movement is detected again for the given tool, the moment when the movement is determined to have resumed can be recorded as the end of event $TO_1$, and the corresponding duration of $T_{TO1}$ can then be extracted.

Note that it can be difficult to determine the exact cause of surgical timeout $TO_1$ solely based on the endoscope video images. For example, the lack of tool movement in the endoscope video can also be associated with other types of timeout events, such as waiting for a collaborating surgeon to arrive. In some embodiments, the exact nature of the detected timeout event $TO_1$ can be further predicted or verified based on the recorded OR audio signals during the same time period as timeout event $TO_1$. Furthermore, these visual and audio data sources can also be used collaboratively with wall and/or ceiling camera videos to determine the exact nature of the timeout $TO_1$.

As another example of a surgical timeout event, phase $P_3$ in surgical procedure 200 is shown to include a second surgical timeout event $TO_2$ when the surgeon is teaching the residents who are observing surgical procedure 200. Because event $TO_2$ happens within phase $P_3$ when the endoscope video is available, the event $TO_2$ can also be detected based on the lack of surgical tool movement in the endoscope video images, and the corresponding duration $T_{TO2}$ can be extracted between the moment when the tool is determined to have stopped moving and the moment when the tool is determined to begin moving again. In practice, although it can be difficult to determine the exact type of surgical timeout $TO_2$ solely based on the video images, the nature of the detected event $TO_2$ can be predicted or verified based on the recorded OR audio signals during the same time period as timeout event $TO_2$.

As yet another example of a non-surgical event taking place during a given surgical phase, phase $P_2$ in surgical procedure 200 is shown to include a tool exchange event EX1 when one surgical tool is taken out of the patient's body and another tool is brought into the patient's body. The event corresponds to a time period designated as $T_{EX1}$. Note that, in addition to the time needed to remove one tool and bring in another tool, $T_{EX1}$ can also include time that the surgeon has to wait for the new tool to be brought to the OR and made ready for use. Because event EX1 happens within phase $P_2$ when the endoscope video is available, the event can be detected by analyzing the endoscope video, and the corresponding duration $T_{EX1}$ can be extracted. However, the detection of event EX1 and the estimation of $T_{EX1}$ can also be based on a collaborative analysis of the endoscope video and videos from the ceiling and wall cameras.

Note that the above-described various non-surgical events within a given surgical phase further break up that phase into a set of surgical segments, wherein the sum of the set of segments corresponds to the actual surgical procedure duration within the given phase, and the sum of all of the surgical segments from all of the phases corresponds to the actual surgical procedure duration of the exemplary surgical procedure 200. However, instead of predicting for each of the surgical segments and calculating the sum, some embodiments detect and estimate the two patient preparation times, various OOB times, various non-surgical times within each surgical phase, and then obtain the overall non-surgical time as the sum of the above. The actual surgical procedure duration is then obtained by excluding the overall non-surgical time from the duration of the overall surgical procedure 200.

Referring still to FIG. 2, note that immediately after the last OOB event $T_{OOB4}$ is the post-surgery patient assistant (i.e., second patient preparation time) $T_{prep2}$, which begins at $t_{endo5}$ when the endoscope video stops and ends at $t_{wo}$ when the patient is wheeled out of the OR. This is the final time period in the full surgical procedure 200 after the final step of the surgical procedure is completed (though the surgeon may or may not have left the OR). During this time period the surgical support team performs necessary steps to complete the overall surgical procedure, such as closing up the incisions in the patient, cleaning up the patient's body (e.g., removing an IV line), transferring the patient from the surgical platform to a wheeled bed, and finally wheeling the patient out of the OR. During the event of $T_{prep2}$, the endoscope video ended. However, like the first preparation time $T_{prep1}$, $T_{prep2}$ can also be determined by analyzing the videos from wall and/or ceiling cameras. In some embodiments, the second preparation time $T_{prep2}$ can be determined by combining the pressure sensor data from the surgical platform with the information from the wall/ceiling camera videos.

Eventually, when the patient is being wheeled out of the OR, the doorway sensor can record the final moment $t_{wo}$ of the full surgical procedure 200. Hence, the overall duration $P_{TOT}$ or the total OR time of the full surgical procedure 200 can be expressed as:

$$P_{TOT} = t_{wo} - t_{wi}.$$

Finally, the actual procedure duration PACT of the full surgical procedure 200 can be computed by excluding all of the above-described non-surgical times from the overall duration $P_{TOT}$:

$$P_{ACT} = P_{TOT} - (T_{prep1} + T_{prep2} + T_{OOB1} + T_{OOB2} + T_{OOB3} + T_{OOB4} + T_{TO1} + T_{TO2} + T_{EX1}).$$

Note that one of the applications of identifying OOB events during a surgical procedure is that the identified OOB events can be used to facilitate HIPAA-compliant surgical video editing. During an OOB event, the endoscope camera can be pointed to various subjects to trigger privacy violations, such as a whiteboard in the OR with patient information, a patient, or surgical support staff. Traditionally, to edit out such OOB segments from recorded surgical videos, HIPAA-compliance experts are hired to watch the videos, identify those OOB segments, and have the video segments blurred out. The disclosed technique to automatically identify OOB events can make HIPAA-compliant video editing a fully automated process.

Figure 3:
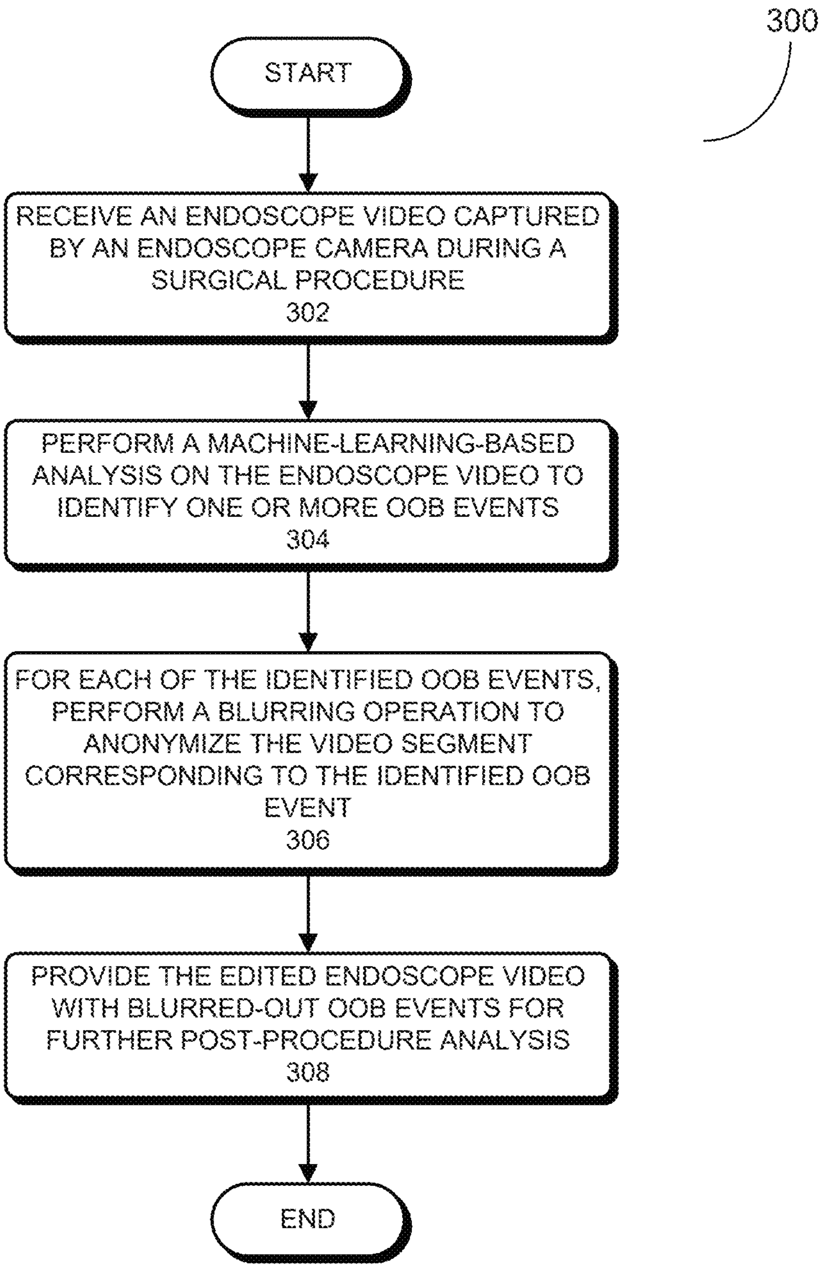
FIG. 3 presents a flowchart illustrating an exemplary process for performing automatic HIPAA-compliant video editing in accordance with some embodiments described herein.

FIG. 3 presents a flowchart illustrating an exemplary process 300 for performing automatic HIPAA-compliant video editing in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 begins by receiving an endoscope video captured by an endoscope camera during a surgical procedure (step 302). In some embodiments, the surgical procedure is a non-robotic minimally invasive surgery (MIS) procedure. In some other embodiments, the surgical procedure is a robotic surgical procedure. Next, process 300 performs a machine-learning-based analysis on the endoscope video to identify one or more OOB events (step 304). As mentioned above, an OOB event is defined as a time period when the endoscope is taken out of the patient's body while the endoscope camera continues to record. Hence, identifying an OOB event would require identifying two transitional events: (1) when the endoscope camera is being taken out of the patient's body; and (2) when the endoscope camera is being placed back into the patient's body. Note that each of these transitional events can be detected based on a given pattern in a sequence of video images. For example, the beginning of the OOB event can be identified based on a sequence of video images depicting when the endoscope camera is being pulled from the patient's body to outside of the patient's body. Within the sequence of images, the identifiable pattern can include multiple frames initially showing an anatomy inside the body, followed by multiple frames of dark images, which are further followed by video frames showing various objects and/or personnel in the OR. Similarly, the end of an OOB event can be identified based a sequence of images made up of multiple frames initially showing various objects and/or personnel in the OR, followed by multiple frames of dark images, which are then followed by multiple frames displaying an anatomy inside the body. In some embodiments, a machine-learning model can be trained to detect a first pattern indicating the beginning of an OOB event based on a first sequence of video frames; and a second pattern indicating the end of an OOB event based on a second sequence of video frames. For each of the identified OOB events, process 300 next performs a blurring operation to anonymize the video segment corresponding to the identified OOB event (step 306). Process 300 subsequently provides the edited endoscope video with blurred-out OOB events for further post-procedural analysis (step 308).

Note that the endoscope videos produced during the surgical procedure are often the best data source for post-procedural analysis, including performing machine-learning-based analysis. Using machine-learning and/or computer-vision analysis tools, an endoscopic video can be used to detect and recognize surgical tools and determine when a surgical tool is actually in contact with the tissue and whether that tool is actually moving. Based on such analyses, the endoscopic video can be used to determine various OOB events that have taken place during the surgical procedure.

The endoscope videos can also be used to identify tool exchange events, i.e., based on performing computer-vision and/or machine-learning-based tool detection and recognition analyses. The endoscope videos can additionally be used to identify surgical timeouts, e.g., by identifying static scenes within the videos indicating various timeout events, such as OR room chats/discussions, waiting for collaborating surgeons, among others. More details of surgical tool detection based on surgical video analysis are described in a related patent application Ser. No. 16/129,593, the contents of which are incorporated by reference herein. As described above, the endoscope videos can also be used to identify a switching time between the robotic phase and the laparoscopic phase of a hybrid surgical procedure.

Furthermore, the endoscope video can be used to perform surgical phase segmentation, i.e., segmenting a surgical procedure into a set of predefined phases, wherein each phase represents a particular stage of the surgical procedure that serves a unique and distinguishable purpose in the entire surgical procedure. More details of the surgical phase segmentation based on surgical video analysis are described in a related patent application Ser. No. 15/987,782, the contents of which are incorporated by reference herein. Note that the set of phases $P_1$, $P_2$, and $P_3$ associated with surgical procedure 200, which are separated by the set of OOB events, is different from the set of pre-defined phases generated by the surgical phase segmentation procedure. In fact, it is not necessary to perform the surgical phase segmentation in order to identify the various non-surgical events. However, segmenting a given surgical procedure into the set of pre-defined phases allows for associating each identified non-surgical event with a given pre-defined phase. Because these non-surgical events generally mean delays in a surgical procedure, knowing which pre-defined phases include which identified non-surgical-related events can significantly improve understanding of a given surgical procedure. For example, identifying which pre-defined surgical phase contains the highest number of identified delays can indicate a deficiency in the surgeon's skill.

In some embodiments, videos from wall and ceiling cameras capture events taking place inside the OR, such as personnel (both the surgeon and the support staff) movements. The captured personnel movements can be used as a direct indicator and/or analyzed using image processing tools to identify tool exchange events, OOB events, certain types of timeout events, and switching between robotic and laparoscopic phases.

In some embodiments, pressure sensor data from the tips or jaws of the surgical tools can be used collaboratively with the endoscope video to reinforce the detection of some timeout events. For example, after detecting a timeout/static event based on the endoscope video, the starting time and the ending time of the static event can be verified based on the pressure sensor data. A person skilled in the art will appreciate that the pressure data from the tool tip sensor can indicate when the tool tip is actually in touch with the tissue and when the tool tip is not touching the tissue. The timestamps associated with the pressure data can then be used to validate the extracted timestamps for the static event based on the endoscope video.

In some embodiments, the pressure sensor data from surgical tool tips can also be used collaboratively with the endoscope video to detect and determine the time periods for some timeout events. For example, the endoscope video can be used as the first data source to detect a segment of the video when the tool(s) in the FOV is not moving (e.g., in combination with observing the pulsing of the tissue). Next, the pressure sensor data from the tool tips around the times of the detected timeout event can be used to pinpoint the beginning (e.g., when the pressure decreases to zero) and the end (e.g., when the pressure increases from zero to a significant value) of the timeout event. Note that using only one of the two data sources, i.e., either detecting from the endoscope video that the tool is not moving, or detecting from the pressure sensor that there is no pressure at the tool tip, may be insufficient to determine whether the tool is completely static. By combining these two data sources, the output based on the collaborative information can lead to much higher confidence levels in the accuracy of the detection.

In some embodiments, the pressure sensors on the patient's bed can be used to detect repositioning of the tools. For example, when the initial positioning of the surgical tools and holes/ports in the body are determined to be improper to access certain anatomy, an additional hole/port in the body may need to be created. When this happens, the camera can usually remain in place, but one or more surgical tools may need to be repositioned. This repositioning may be categorized as a type of surgical timeout because while the surgeon is trying to figure out a proper tool placement, no tool-tissue interaction is happening. Note that if the repositioning requires repositioning of the patient on the surgical platform, the pressure sensor on the platform can detect a change in pressure as a result. However, if the repositioning requires little change of the patient's position, it is more dependable to combine the pressure sensor data with the videos from the wall and ceiling cameras to actually see the repositioning process.

Figure 4:
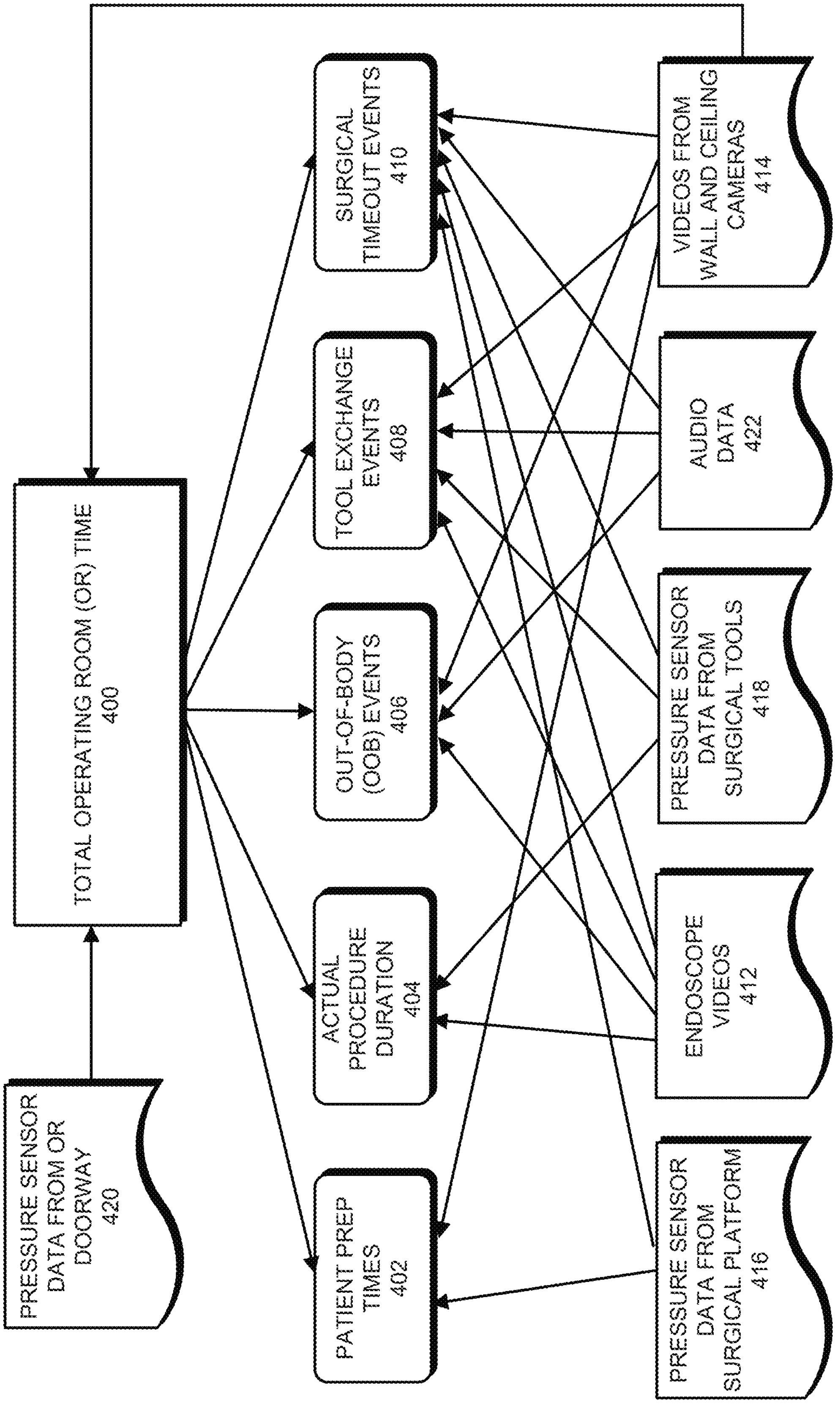
FIG. 4 presents a block diagram illustrating the interrelationships between various types of events that constitute the total OR time of a surgical procedure and the set of data sources available inside the OR during the surgical procedure in accordance with some embodiments described herein.

FIG. 4 presents a block diagram illustrating the interrelationships among various types of events 402-410 that constitute the total OR time 400 of a surgical procedure and the set of data sources 412-422 available inside the OR during the surgical procedure in accordance with some embodiments described herein. As can be seen in FIG. 4, total OR time 400 includes patient preparation times 402, actual procedure duration 404, OOB events 406, tool exchange events 408, and surgical timeout events 410. The set of data sources includes endoscope videos 412, videos 414 from wall and ceiling cameras, pressure sensor data 416 from the surgical platform, pressure sensor data 418 from the surgical tools, pressure sensor data 420 from the OR doorway, and OR audio data 422. Note that each arrow linking a given type of event and a given data source represents that the given data source can be used, either on its own or in conjunction with other data sources, to detect/identify the given type of event from the full surgical procedure.

As described above, total OR time 400 can be determined based on pressure sensor data 420 from the OR doorway, based on the videos 414 captured by the wall/ceiling cameras, or based on a combination of the pressure sensor data 420 and videos 414. For example, if the total OR time 400 determined based on pressure sensor data 420 is unreasonably short, videos 414 from the wall/ceiling cameras can be used to verify or make corrections to the total OR time 400 determined solely based on pressure sensor data 420. Note that determining total OR time 400 is a relatively straightforward process and typically does not require using computer-vision or machine-learning techniques.

As further described above, patient preparation times 402 can include the pre-surgery preparation time $T_{prep1}$ and the post-surgery preparation time $T_{prep2}$, and both can be directly determined based on videos 414 from the wall and/or ceiling cameras. In some embodiments, these $t_{wo}$ patient preparation times 402 can also be determined based on the pressure sensor data 416 from the surgical platform. For example, to determine the first preparation time $T_{prep1}$, pressure sensor data 416 from the surgical platform can be analyzed to determine when the sensor data has increased from zero (without patient) to a significantly higher value (when the patient is transferred onto the surgical platform), and has stabilized (e.g., after positioning the patient on the surgical platform). Next, $T_{prep1}$ can be determined as the time period between wheeled-in time $t_{wi}$ and the moment when the pressure data on the surgical platform stabilizes. Similarly, to determine the second preparation time $T_{prep2}$, pressure sensor data 416 from the surgical platform can be analyzed to determine when the data has decreased from a higher value (when the patient is still lying on the surgical platform) to a significantly lower value or zero (when the patient is removed from the surgical platform). Next, the $T_{prep2}$ can be determined as the time between the wheeled-out time $t_{wo}$ and the time when the pressure data on the surgical platform becomes zero. In some embodiments, $T_{prep1}$ and $T_{prep2}$ can be determined based on the combination of the pressure sensor data 416 from the surgical platform and videos 414 captured by the wall/ceiling cameras.

As also described above, OOB events 406 can include OOB events during the actual surgical procedure (or "in-procedure OOB events" hereinafter), an initial OOB event at the beginning of the actual surgical procedure, and a final OOB event at the end of the actual surgical procedure. Moreover, each of the in-procedure OOB events can be identified within the total OR time 400 based on analyzing endoscope videos 412. In some embodiments, to identify a given in-procedure OOB event from total OR time 400, a machine-learning model can be applied to endoscope videos 412 to identify the beginning of the OOB event based on a first sequence of video images, and to identify the end of the OOB event based on a second sequence of video images. Note that prior to applying the machine-learning model to identify OOB events from the total OR time 400, the model can be trained to classify a sequence of video images as one of: (1) the beginning of an in-procedure OOB event; (2) the end of an in-procedure OOB event; and (3) neither of the above.

Also described earlier, if the endoscope camera is turned on prior to the initial insertion of the endoscope into the patient's body, an initial OOB event exists and needs to be detected. Note that to identify the initial OOB event from the total OR time 400, only the end of the initial OOB event needs to be detected. In some embodiments, the same machine-learning model used for detecting in-procedure OOB events can be applied to the beginning portion of the endoscope video to determine when the endoscope is initially inserted into the patient's body based on a sequence of video images. Next, the initial OOB event can be calculated as the time between the beginning of an endoscope video 412 and the determined initial insertion time.

Similarly, if the endoscope camera remains turned on for some time after the final removal of the endoscope from the patient's body, a final OOB event exists and needs to be detected. Note that to identify the final OOB event from the total OR time 400, only the beginning of the final OOB event needs to be detected. In some embodiments, the same machine-learning model used for detecting in-procedure OOB events can be applied to the final portion of an endoscope video 412 to determine when the endoscope is finally removed from the patient's body based on a sequence of video images. Next, the final OOB event can be calculated as the time between the end of the endoscope video 412 and the determined final endoscope removal time.

Note that all of the above OOB events can also be directly identified based on videos 414 from the wall/ceiling cameras. For example, for an in-procedure OOB event related to lens cleaning, one or more videos 414 captured in the OR during the surgical procedure may capture the event including the moment when the endoscope is taken out of the patient's body and the moment when the endoscope is re-inserted into the patient's body after lens cleaning and camera recalibration. In some embodiments, an in-procedure OOB event can be determined based on the combination of endoscope videos 412 and videos 414 from the wall/ceiling cameras. For example, if analyzing endoscope videos 412 fails to identify either the beginning or the end of an in-procedure OOB event, the corresponding videos 414 can be used to help identify the missing timestamp. More specifically, if analyzing endoscope videos 412 has identified the beginning of an OOB event to, but fails to identify the end of the OOB event $t_e$, videos 414 from the wall and ceiling cameras can be reviewed from the time $t_b$ onward till the point when the endoscope is being re-inserted into the camera port. Similarly, if analyzing endoscope videos 412 has identified the end of the OOB event $t_e$, but fails to identify the beginning of the OOB event $t_b$, videos 414 from the wall and ceiling cameras can be reviewed from the time $t_e$ backward till the point when the endoscope is being removed from the camera port.

Tool exchange events 408 make up another portion of total OR time 400 that does not belong to actual procedure duration 404. As described above, each of the tool exchange events 408 can be determined based on analyzing endoscope videos 412. Because detecting a tool exchange event involves detecting and recognizing multiple surgical tools, a machine-learning-based analysis can be applied to endoscope videos 412, e.g., by individually identifying the beginning and the end of a tool exchange event. For example, a machine-learning-based video analysis tool may continue to detect and recognize a first surgical tool (e.g., a surgical stapler) up until image frame i, but begins to detect and recognize a second surgical tool (e.g., a surgical grasper) starting from image frame i+50. In between image frames i and i+50, no surgical tool is detected from endoscope videos 412. The video analysis tool can then conclude that a tool exchange event 408 has been detected starting from frame i and ending at frame i+50, and a corresponding tool exchange time can also be extracted.

In some embodiments, a tool exchange event 408 can also be detected based on pressure sensor data 418 from tips or jaws of the two surgical tools involved in the tool exchange event. For example, the beginning of the tool exchange event 408 can be determined as the time when the pressure sensor data 418 from the first surgical tool (which is being replaced) goes from a finite value to zero, whereas the end of the tool exchange event 408 can be determined as the time when the pressure sensor data 418 from the second surgical tool (which is replacing the first surgical tool) goes from zero to a finite value. In some embodiments, a tool exchange event 408 can be identified based on the combination of endoscope videos 412 and pressure sensor data 418 from the surgical tools involved in the tool exchange event. In some embodiments, a tool exchange event 408 can also be identified based on the combination of endoscope videos 412, pressure sensor data 418 from the surgical tools involved in the tool exchange event, and videos 414 from the wall and ceiling cameras.

Surgical timeout events 410, such as OR room chats/discussions or waiting for collaborating surgeons, make up for another portion of the total OR time 400 that does not belong to actual procedure duration 404. As described above, during a surgical timeout, the surgeon is not doing anything with a surgical tool in the FOV of an endoscope video; therefore, the surgical tool is idle and the scene appears static in the endoscope video. Hence, each of the surgical timeout events 408 can be identified based on analyzing the corresponding video 412. For example, by analyzing a sequence of images and recognizing that the scene has not changed over a predetermined number of frames (e.g., 20 frames), a timeout event can be identified. Note that often-times the scene of the endoscope video is not completely static due to pulsing of the organs in the FOV. However, the pulsing can be extracted as the background noise, or used as a signature indicating a static scene (when pulsing is the only action).

In some embodiments, a surgical timeout event 410 can also be detected based on pressure sensor data 418 from the surgical tools involved in the event. For example, the beginning of a surgical timeout event 410 can be identified as the time when pressure sensor data 418 from the surgical tool goes from a finite value to zero (i.e., becomes inactive), whereas the end of the surgical timeout event 410 can be identified as the time when pressure sensor data 418 from the surgical tool goes from zero to a finite value (i.e., becomes active again). In some embodiments, a surgical timeout event 410 can be determined based on the combination of the endoscope video 412 and pressure sensor data 418 from the surgical tools involved in the event. In some embodiments, a surgical timeout event 410 can also be determined based on videos 414 from the wall and ceiling cameras.

Note that audio data 422 recorded during total OR time 400 can include verbal exchanges between the surgeon and other people both inside and outside the OR. At any point in time during total OR time 400, audio data 422 provide clues to the ongoing event. Hence, audio data 422 can be used collaboratively with any of the other data sources 412-420 to detect each type of non-surgical event 406-410, or to improve the accuracy and confidence of the detection of such events initially based on data sources 412-420. In some embodiments, processing audio data 422 in collaboration with data sources 412-420 for non-surgical event detection can include performing natural language processing on audio data 422.

As can be seen, the disclosed surgical procedure analysis system allows for identifying and extracting the corresponding duration for each non-surgical event and each type of the described non-surgical events. Once all of the above information is available, the full surgical procedure and the corresponding total OR time duration can be broken up into the different segments described above. The extracted time information of various surgical and non-surgical events can be used to perform in-depth analysis of and provide insight into the corresponding surgical procedure, e.g., by evaluating individually or in combination (e.g., as a combined time of the same type of non-surgical event) to determine its impact on the total OR time (e.g., in term of percentage of total OR time 400). For example, the total recorded tool exchange time can be used to evaluate the impact of tool exchange events on the total OR time. Note that tool recognition information extracted along with detecting tool exchange events can also be used for the purposes of tool inventory, and tracking how many times surgical tools are used or fired. The extracted time information of various surgical and non-surgical events is also correlated to, and therefore can also be used to perform assessments of, the following metrics: OR workflow efficiency; OR cost; Effect on anesthesia dosage; Effect on infection rates; Surgeon skill evaluations; and Surgical procedure outcomes analysis. The results from the above evaluations can then guide the relevant hospitals, surgeons, and surgical support teams to make corrections and adjustments to their OR practices.

Moreover, the time information for a given type of non-surgical event can be used for item-to-item comparisons between different surgical procedures and different surgeons. As a concrete example, for two surgical procedures A and B of the same type performed by two surgeons A and B, the total OR times indicate that surgeon A spends 20 minutes longer in the OR than surgeon B. After extracting various non-surgical events, it is determined that the actual procedure durations of the two procedures are substantially the same. However, procedure A has 20 minutes more in determined overall timeout events than procedure B, e.g., due to the discussions of surgeon A with others in the OR. This analysis can reveal that surgeon A is less efficient as a result of taking too many timeouts.

Figure 5:
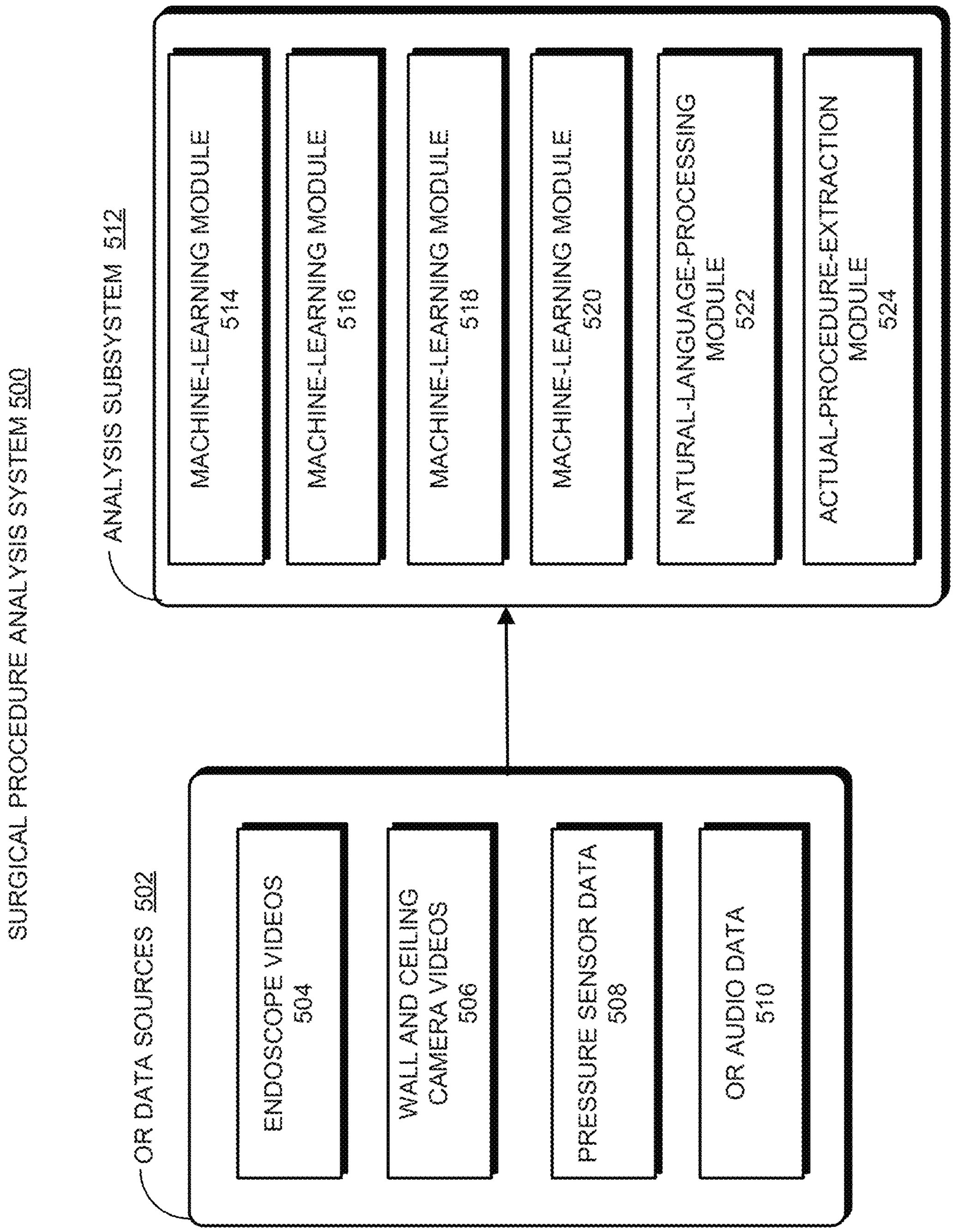
FIG. 5 shows a block diagram of an exemplary surgical procedure analysis system in accordance with some embodiments described herein.

FIG. 5 shows a block diagram of an exemplary surgical procedure analysis system 500 in accordance with some embodiments described herein. As can be seen in FIG. 5, surgical procedure analysis system 500 includes OR data sources 502 that further include endoscope videos 504, wall/ceiling camera videos 506, pressure sensor data 508, and OR audio data 510, each of which is collected inside an OR during a surgical procedure. Note that pressure sensor data 508 can further include pressure sensor data from surgical tool tips or jaws, pressure sensor data from a surgical platform, and pressure sensor data from an OR doorway.

As can be seen in FIG. 5, surgical procedure analysis system 500 further includes a surgical procedure analysis subsystem 512, which is coupled to OR data sources 502 and configured to receive various video, audio and sensor data 504-510 from OR data sources 502 and perform various above-described surgical procedure analyses to break down a total OR time by identifying various disclosed surgical and non-surgical segments/events and extract the duration of each of the identified surgical or non-surgical segments/events. More specifically, surgical procedure analysis subsystem 512 can include a set of machine-learning modules that can be applied to one or more of the data sources 504-510 to identify various surgical and non-surgical events.

For example, these machine-learning modules can include a machine-learning module 514 for identifying a set of OOB events during the total OR time mainly based on endoscope videos 504; a machine-learning module 516 for identifying a set of tool exchange events during the total OR time mainly based on endoscope videos 504; a machine-learning module 518 for identifying a set of surgical timeout events during the total OR time mainly based on endoscope videos 504; and a machine-learning module 520 for identifying a set of actual surgical segments during the total OR time mainly based on endoscope videos 504. These machine-learning modules can also include a natural-language-processing module 522 for analyzing OR audio data 510, and the output from natural-language-processing module 522 can be used by machine-learning modules 514-520 to improve the accuracy of detection of various surgical and non-surgical events. Note that surgical procedure analysis subsystem 512 also includes an actual-procedure-extraction module 524 that can use the output from machine-learning modules 514-520 to extract the actual procedure duration from the total OR time.

Figure 6:
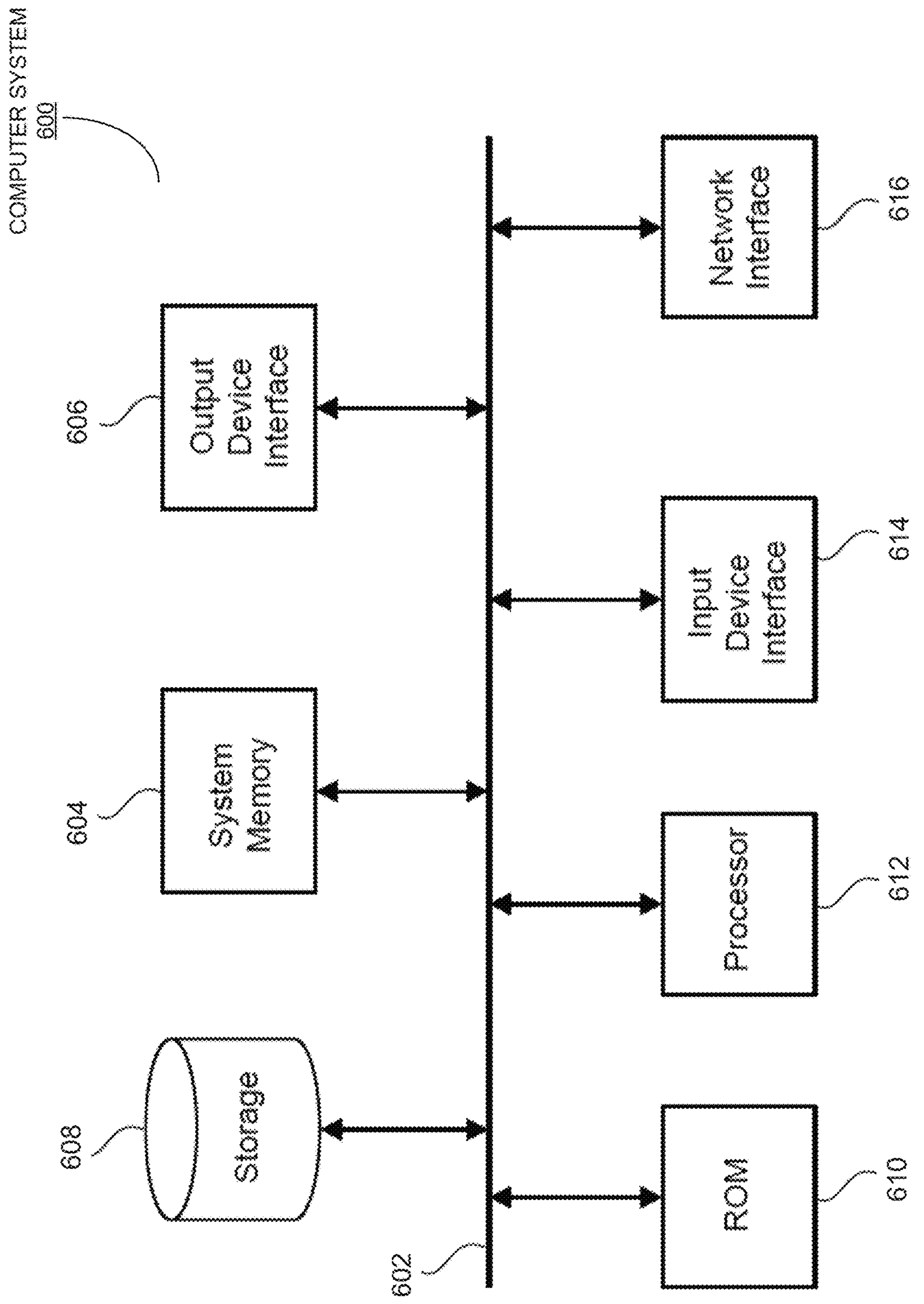
FIG. 6 conceptually illustrates a computer system with which some embodiments of the subject technology can be implemented.

FIG. 6 conceptually illustrates a computer system with which some embodiments of the subject technology can be implemented. Computer system 600 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 600 includes a bus 602, processing unit(s) 612, a system memory 604, a read-only memory (ROM) 610, a permanent storage device 608, an input device interface 614, an output device interface 606, and a network interface 616. In some embodiments, computer system 600 is a part of a robotic surgical system.

Bus 602 collectively represents all system, peripheral, and chipset buses that communicatively connect the numerous internal devices of computer system 600. For instance, bus 602 communicatively connects processing unit(s) 612 with ROM 610, system memory 604, and permanent storage device 608.

From these various memory units, processing unit(s) 612 retrieves instructions to execute and data to process in order to execute various processes described in this patent disclosure, including the above-described surgical procedure analyses to detect/identify various disclosed surgical and non-surgical events, extract the durations of the identified events, and extract the actual procedure duration from the total OR time described in conjunction with FIGS. 1-5. The processing unit(s) 612 can include any type of processor, including but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 612 can be a single processor or a multi-core processor in different implementations.

ROM 610 stores static data and instructions that are needed by processing unit(s) 612 and other modules of the computer system. Permanent storage device 608, on the other hand, is a read-and-write memory device. This device is a non-volatile memory unit that stores instructions and data even when computer system 600 is off. Some implementations of the subject disclosure use a mass-storage device (such as a magnetic or optical disk and its corresponding disk drive) as permanent storage device 608.

Other implementations use a removable storage device (such as a floppy disk, flash drive, and its corresponding disk drive) as permanent storage device 608. Like permanent storage device 608, system memory 604 is a read-and-write memory device. However, unlike storage device 608, system memory 604 is a volatile read-and-write memory, such as a random access memory. System memory 604 stores some of the instructions and data that the processor needs at runtime. In some implementations, various processes described in this patent disclosure, including the processes of detecting/identifying various disclosed surgical and non-surgical events, extracting the durations of the identified events, and extracting the actual procedure duration from the total OR time described in conjunction with FIGS. 1-5, are stored in system memory 604, permanent storage device 608, and/or ROM 610. From these various memory units, processing unit(s) 612 retrieves instructions to execute, and data to process in order to execute the processes of some implementations.

Bus 602 also connects to input and output device interfaces 614 and 606. Input device interface 614 enables the user to communicate information to and select commands for the computer system. Input devices used with input device interface 614 include, for example, alphanumeric keyboards and pointing devices (also called "cursor control devices"). Output device interface 606 enables, for example, the display of images generated by computer system 600. Output devices used with output device interface 606 include, for example, printers and display devices, such as cathode ray tubes (CRT) or liquid crystal displays (LCD). Some implementations include devices such as a touch-screen that functions as both input and output devices.

Finally, as shown in FIG. 6, bus 602 also couples computer system 600 to a network (not shown) through a network interface 616. In this manner, the computer can be a part of a network of computers (such as a local area network ("LAN"), a wide area network ("WAN"), an intranet, or a network of networks, such as the Internet. Any or all components of computer system 600 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. The terms "disk" and "disc," as used herein, include compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can, in some cases, be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for digitally processing an endoscope video of a full surgical procedure performed on a patient, the method comprising the following operations performed by a digital processor:

receiving operating room (OR) data collected during the full surgical procedure, wherein the OR data includes an endoscope video captured by an endoscope during an overall procedure duration of the full surgical procedure;

analyzing, by a machine-learning, ML, model the OR data for the overall procedure duration of the full surgical procedure, including detecting all tool-tissue interaction events during the overall procedure duration, and identifying one or more out of body events in which the endoscope is taken out of the body of the patient;

extracting the duration of each of the one or more out of body events; and for each of the one or more out of body events, blurring a segment of the endoscope video that corresponds to the out of body event to anonymize the segment.

2. The computer-implemented method of claim 1 wherein the OR data further comprises audio recorded inside the OR during the full surgical procedure, and the method further comprises the digital processor analyzing for the overall procedure duration the endoscope video and the recorded audio to detect all intervals in which the endoscope video becomes static and the recorded audio contains a discussion between a surgeon and another person.

3. The computer-implemented method of claim 1 wherein the OR data further comprises audio recorded inside the OR during the full surgical procedure, a video captured by a wall camera or a ceiling camera inside the OR during the full surgical procedure, and sensor data collected inside the OR during the full surgical procedure, the sensor data comprises one or more of:

pressure sensor data collected from surgical tools involved in the full surgical procedure;

pressure sensor data collected from a surgical platform inside the OR; and pressure sensor data collected from a doorway of the OR, the method further comprising the digital processor analyzing, for the overall procedure duration, the recorded audio, the video captured by the wall camera or the ceiling camera, and the sensor data, in order to identify the one or more out of body events.

4. The computer-implemented method of claim 1 wherein the ML model identifies the beginning of the out of body event based on a first sequence of video images in the endoscope video, and identifies the end of the out of the body event based on a second sequence of video images in the endoscope video.

5. The computer-implemented method of claim 1 wherein the out of body event coincides with:

cleaning a lens of the endoscope which blocks an endoscopic view;

changing the lens from one scope size to another scope size; or switching during the full surgical procedure from a robotic surgical system to a laparoscopic surgical system.

6. The computer-implemented method of claim 1 wherein the ML model further analyzes the OR data for the overall procedure duration of the full surgical procedure, to detect:

an initial out of body event at a beginning of the surgical procedure when the endoscope is turned on prior to being inserted into the patient's body; and a final out of body event at an end of the surgical procedure when the endoscope remains turned on even after a completion of the surgical procedure by a surgical support team, the method further comprising the digital processor blurring a plurality of segments of the endoscope video that correspond to the initial out of body event and the final out of body event, to anonymize the plurality of segments.

7. A system for digitally processing an endoscope video of a full surgical procedure performed on a patient, the system comprising:

a processor; and a memory coupled to the processor, wherein the memory stores instructions that, when executed by the processor, cause the system to:

receive operating room (OR) data collected during the surgical procedure, wherein the OR data includes an endoscope video captured by an endoscope during an overall procedure duration of the surgical procedure;

analyze, by a machine-learning model, ML model, the OR data for the overall procedure duration of the surgical procedure, including detecting all tool-tissue interaction events during the overall procedure duration, and identifying one or more out of body events in which the endoscope is taken out of the body of the patient;

extract the duration of each of the one or more out of body events; and for each of the one or more out of body events, blur a segment of the endoscope video that corresponds to the out of body event to anonymize the segment.

8. The system of claim 7 wherein the OR data further comprises audio recorded inside the OR during the full surgical procedure, and the processor analyzes for the overall procedure duration the endoscope video and the recorded audio to thereby detect all intervals in which the endoscope video becomes static and the recorded audio contains a discussion between a surgeon and another person.

9. The system of claim 7 wherein the OR data further comprises audio recorded inside the OR during the full surgical procedure, a video captured by a wall camera or a ceiling camera inside the OR during the full surgical procedure and sensor data collected inside the OR during the full surgical procedure, the sensor data comprises one or more of:

pressure sensor data collected from surgical tools involved in the full surgical procedure;

pressure sensor data collected from a surgical platform inside the OR; and pressure sensor data collected from a doorway of the OR, wherein the processor identifies the one or more out of body events based on further analysis of, for the overall procedure duration, the recorded audio, the video captured by the wall camera or the ceiling camera, and the sensor data.

10. The system of claim 7 wherein the ML model identifies the beginning of the out of body event based on a first sequence of video images in the endoscope video, and identifies the end of the out of the body event based on a second sequence of video images in the endoscope video.

11. The system of claim 7 wherein the out of body event coincides with:

cleaning a lens of the endoscope which blocks an endoscopic view;

changing the lens from one scope size to another scope size; or switching during the full surgical procedure from a robotic surgical system to a laparoscopic surgical system.

12. The system of claim 7 wherein the ML model further analyzes the OR data for the overall procedure duration of the full surgical procedure, to detect:

an initial out of body event at a beginning of the surgical procedure when the endoscope is turned on prior to being inserted into the patient's body; and a final out of body event at an end of the surgical procedure when the endoscope remains turned on even after a completion of the surgical procedure by a surgical support team, and wherein the processor further blurs a plurality of segments of the endoscope video that correspond to the initial out of body event and the final out of body event, to anonymize the plurality of segments.

13. A computer readable medium comprising stored instructions to be executed by a processor for digitally processing an endoscope video of a full surgical procedure performed on a patient, wherein the processor executes the instructions to:

receive operating room (OR) data collected during the surgical procedure, wherein the OR data includes an endoscope video captured by an endoscope during an overall procedure duration of the surgical procedure;

analyze, by a machine-learning model, ML model, the OR data for the overall procedure duration of the surgical procedure, including detecting all tool-tissue interaction events during the overall procedure duration, and identifying one or more out of body events in which the endoscope is taken out of the body of the patient;

extract the duration of each of the one or more out of body events; and for each of the one or more out of body events, blur a segment of the endoscope video that corresponds to the out of body event to anonymize the segment.

14. The computer readable medium of claim 13 wherein the OR data further comprises audio recorded inside the OR during the full surgical procedure, and the instructions configure the processor to analyze for the overall procedure duration the endoscope video and the recorded audio to thereby detect one or more intervals in which i) the endoscope video becomes static and ii) the recorded audio contains a discussion between a surgeon and another person.

15. The computer readable medium of claim 13 wherein the OR data further comprises audio recorded inside the OR during the full surgical procedure, a video captured by a wall camera or a ceiling camera inside the OR during the full surgical procedure and sensor data collected inside the OR during the full surgical procedure, the sensor data comprises one or more of:

pressure sensor data collected from surgical tools involved in the full surgical procedure;

pressure sensor data collected from a surgical platform inside the OR; and pressure sensor data collected from a doorway of the OR, wherein the instructions configure the processor to identify the one or more out of body events based on further analysis of, for the overall procedure duration, the recorded audio, the video captured by the wall camera or the ceiling camera, and the sensor data.

16. The computer readable medium of claim 13 wherein the ML model identifies the beginning of the out of body event based on a first sequence of video images in the endoscope video, and identifies the end of the out of the body event based on a second sequence of video images in the endoscope video.

17. The computer readable medium of claim 13 wherein the out of body event coincides with:

cleaning a lens of the endoscope which blocks an endoscopic view;

changing the lens from one scope size to another scope size; or switching during the full surgical procedure from a robotic surgical system to a laparoscopic surgical system.

18. The computer readable medium of claim 13 wherein the instructions configure the processor to use the ML model to further analyze the OR data, for the overall procedure duration of the full surgical procedure, to detect:

an initial out of body event at a beginning of the surgical procedure when the endoscope is turned on prior to being inserted into the patient's body; and a final out of body event at an end of the surgical procedure when the endoscope remains turned on even after a completion of the surgical procedure by a surgical support team, and wherein the processor further blurs a plurality of segments of the endoscope video that correspond to the initial out of body event and the final out of body event, to anonymize the plurality of segments.

* * * * *